United States Patent [19]
Nightengale

[11] Patent Number: 5,779,642
[45] Date of Patent: Jul. 14, 1998

[54] INTERROGATION DEVICE AND METHOD

[76] Inventor: Christopher Nightengale, 6303 E. Jamison Cir. South, Englewood, Colo. 80112

[21] Appl. No.: 801,562

[22] Filed: Feb. 18, 1997

Related U.S. Application Data

[63] Continuation-in-part of Ser. No. 585,924, Jan. 16, 1996.

[51] Int. Cl.⁶ ............................................. A61B 8/12
[52] U.S. Cl. .............................. 600/461; 600/554
[58] Field of Search ............................. 600/461, 546, 600/554

[56] References Cited

U.S. PATENT DOCUMENTS

| | | |
|---|---|---|
| 3,830,226 | 8/1974 | Staub et al. |
| 4,501,278 | 2/1985 | Yamaguchi et al. |
| 4,515,168 | 5/1985 | Chester et al. |
| 4,824,433 | 4/1989 | Marzetal |
| 4,887,606 | 12/1989 | Yock et al. ............... 128/662.05 |
| 4,962,766 | 10/1990 | Herzon |
| 5,284,153 | 2/1994 | Raymond et al. ............ 128/741 |
| 5,306,236 | 4/1994 | Blumenfeld et al. ......... 600/546 X |
| 5,311,871 | 5/1994 | Yock |

*Primary Examiner*—Francis Jaworski
*Attorney, Agent, or Firm*—Sheridan Ross P.C.

[57] ABSTRACT

An interrogation device is used to locate a nerve within the body. The device uses a piezoelectric crystal to locate a pulsing vessel proximate with the nerve. As the device is guided toward the nerve, it can emit an electric signal to stimulate the nerve. The operator can then watch for any physical reaction from the patient in response to nerve stimulation. As the device closes upon the nerve, pressure is applied with the needle to the vessel, thus compressing the vessel, diminishing the doppler response. Once the surface of the nerve is located, it can be accurately anesthetized.

9 Claims, 3 Drawing Sheets

INTERROGATION DEVICE AND METHOD

RELATED APPLICATIONS

This application is a continuation in part of U.S. patent application Ser. No. 08/585,924 filed on Jan. 16, 1996.

TECHNICAL FIELD OF THE INVENTION

The present invention relates to an interrogation device and specifically a guiding and localizing device which accurately positions a puncture needle proximate a nerve and a vessel having flowing blood cells, such as a neurovascular bundle, for use in regional anesthesia procedures.

BACKGROUND OF THE INVENTION

The present invention relates to an interrogation device and specifically a Doppler-guided nerve stimulator device which accurately localizes and positions a puncture needle or other surgical probe into a neurovascular bundle or near a nerve. This invention has application in a variety of medical procedures, and has particular utility in regional anesthesia procedure. The neurovascular bundle includes a fibrous sheath or fascial compartment surrounding a nerve and a vessel. The ability to perform regional anesthesia requires the very precise placement of the appropriate drug inside of a neurovascular bundle innervating the region to be anesthetized. Previously, localization and puncture of the neurovascular bundle has been dependent on the skill of the operator either in guiding an appropriately beveled needle, or in following the motor responses elicited by a nerve stimulator attached to a conductive electrode. Devices of this latter type are known as nerve stimulator electrodes. However, as listed in Plexus Anesthesia Vol. 1 by A. Winnie M.D., because the neurovascular bundle travels near vital structures, these devices are associated with operator error and well recognized morbidity and mortality. For example, in the upper extremities the neurovascular bundle has a posterior, superior position in relation to the clavicle. Closely apposed to the bundle is the pleura and substance of the lung. Inaccurate placement of a needle into the lung can result in pneumothorax while inadvertent injury to a vessel can result in hemothorax. Long term nerve injuries after blind injection into the neurovascular bundle are well known. Separate but equally serious injuries can occur to structures adjacent to the neurovascular bundle when the anatomy is obscured, minimize nearby structure or vascular injury and allow easy confirmation of position within the neurovascular bundle.

One example of an interrogation device is shown in U.S. Pat. No. 3,830,226 to Staub et al. This device is a variable output nerve locator that permits stimulation of an exposed nerve by the application of electrical energy to the nerve. This device however does not use a guide needle, will not allow administration of medications or the introduction of other instruments into the neurovascular bundle, and requires exposure of the nerve surgically. A second example is shown in U.S. Pat. No. 4,824,433 to März et al. März discloses a puncturing and catheterizing device for the human or animal body which uses a conductive puncture needle and a surrounding cannula. The device is specifically intended for nerve tracts and allows the use of an attached nerve stimulator. This device allows only electrical stimulation to be used to provide directional information and does not allow the attachment of different sensors to the puncture needle and cannula. A third and different type of device is disclosed in U.S. Pat. No. 4,887,606 by Yock for cannulation of a vessel. This device relies upon an ultrasound transducer attached to the tip of a trocar positioned within a hollow needle for transmitting and receiving ultrasonic waves through the sharpened end of the needle. The device can be guided in response to the backscattered ultrasound energy reflected from flow within the vessel until the vessel is cannulated. However, the patent does not disclose any means or method of distinguishing the vessel from the neurovascular bundle nor any means or method for locating or avoiding the nerves contained within a bundle should it be used for cannulation of a vessel contained within a neurovascular bundle. Nor does the device assure localization of the sharpened needle tip within a neurovascular bundle or in close proximity to a selected nerve. It also does not allow the addition of other sensors such as a nerve stimulator or allow the use of a bipolar stimulator design.

SUMMARY OF THE INVENTION

The present invention takes advantage of the close proximity of blood carrying vessels, such as arteries and veins, and nerves. One example is known as a neurovascular bundle where vessels and nerves are enclosed within a facial covering. The invention facilitates localization of the bundle, confirms puncture of the fascial sheath and assures placement of a needle adjacent to the nerves to be anesthetized.

The objects of the invention are to:

1. Provide an apparatus for safely localizing a nerve or nerve bundle having a known anatomical relationship with a vessel.
2. Facilitate localization of the neurovascular bundle by targeting with Doppler ultrasound the flow passing within an artery or vein enclosed within the surrounding fascial covering.
3. Assure placement of a guide needle in close proximity to the nerves to be anesthetized by observing a particular motor response elicited by the use of nerve stimulation.
4. Confirm puncture of the fascial sheath by altering an observed muscle response to nerve stimulation or through ultrasound auditory information or a combination of both.
5. Allow access to the neurovascular bundle for placement of drugs, guidewires, catheters, and other instruments after assuring placement of the guide needle within the neurovascular bundle.
6. The invention should minimize the possibility of injury to structures adjacent to the neurovascular bundle.

These objects are achieved by enclosing an ultrasound source within a nerve stimulator electrode. In a preferred embodiment, both the nerve stimulator electrode and the enclosed piezoelectric crystal are attached to the tip of a support rod that fits within a hollow guide needle and is removable from the guide needle. The piezoelectric crystal is excited by an electrical RF signal in the range of 2–20 MHz and emits ultrasonic energy in a direction having a significant component along the blood vessel axis. Individual blood cells represent discrete scattering elements which independently scatter a small fraction of the ultrasound energy back in the direction of the piezoelectric transducer. This backscattered radiation exhibits two frequency shifts, known as the Doppler shift, due to the relative motion of the cells and the transducer. The change in frequency may be either an increase, if the direction of blood flow is toward the probe, or a decrease, if the flow is directed away from the probe. In either case, the first frequency shift occurs between the transducer and the reference frame of the cell, which receives the signal and imparts a first frequency shift (for small changes).

$$fd/fo = (u/v)\cos\theta$$

where fd=the Doppler frequency shift
of=the source frequency
u=the cell velocity
v=the velocity of sound in blood
θ=angle between the blood flow vector and the normal to the acoustic wavefront The second shift occurs at the re-transmission (backscattering) of the signal from the moving cell which is ultimately received by the transducer. The total fractional change in frequency as received is thus:

$$fd/of = 2u\cos\theta/(v+u) \sim 2(u/v)\cos\theta \text{ for } v \gg u$$

The piezoelectric crystal supplies ultrasound energy through the hollow tip of the guide needle and can receive backscattered ultrasound signals which are Doppler shifted from flow sources within the neurovascular bundle. This backscattered ultrasound signal is mixed with the transmitted signal in such a way that a difference signal having a frequency in the audio range is produced, amplified and provided to the operator and directs the operator in the direction of the flow source while the operator watches for a motor response elicited by the nerve stimulator electrode. This electrode transfers current from nerve stimulator circuitry through electrical connections at the base of the support rod to tissue near the tip of the needle and activates a motor response from muscle innervated by the stimulated nerve. The nerve stimulator electrode acts as the common ground for the piezoelectric crystal and the current driver circuitry that stimulates the nerve. Placing the anode at the tip of the support rod and close to the nerve allows the minimal amount of stimulating current to excite the nerve while decreasing errors in placement due to surrounding muscle response. Anode excitation also decreases the amount of current necessary to stimulate the nerve. The removable transducer design also allows placement of catheters, guidewires, other instruments, and drugs within the neurovascular bundle after confirmation of needle placement. Confirmation of needle position within the bundle can be assured in three ways; by using a B-bevel needle as the guide needle, which supplies the operator with a high frequency ultrasound signal on passing through the bevel needle as the guide needle, which supplies the operator with a high frequency ultrasound signal on passing through the fibrous fascial covering; by listening for diminished signal intensity from the Doppler ultrasound crystal as the B-bevel guide needle compresses flow within the target vessels in the neurovascular bundle; or by removing the transducer from the guide needle after observing an appropriate muscle response, injecting a small amount of local anesthetic and watching for a reduced motor response to nerve stimulation.

In summary, the nerve stimulator electrode combined with the ultrasound crystal addresses the preceding objects of the invention.

1. The electrode acts as the common ground coupling the circuitry for the dual sensors of the piezoelectric crystal emitting ultrasound energy and the nerve stimulator circuit directing current impulses for nerve localization.
2. The electrode sits at the distal tip of the support rod in close proximity to the tissue being electrically stimulated and precisely directs the current applied to nearby tissue.
3. The electrode can act as the anion for a bipolar versus monopolar nerve stimulator by insulating the surrounding guide needle. This allows a novel single needle bipolar design for nerve stimulation.
4. Filling the annulus of the enclosing guide needle with an ionic electrically conductive solution, such as 0.9 percent (%) NaCl, forms an "ionic" connection between the PZT crystal ground and the nerve stimulator electrode in its function as the ultrasound circuit ground. Simultaneously, the 0.9% NaCl doubles as an acoustic medium transferring ultrasound energy into the surrounding tissue and conducts current from the nerve stimulator circuit into the nearby tissue. This eliminates the need for an electrodisposition connection between the crystal and electrode, although a conventional electrode to crystal electrical connection is also appropriate.

BRIEF DESCRIPTION OF THE DRAWINGS

For a more complete understanding of the present invention, and for further details and advantages thereof, reference is now made to the following Detailed Description taken in conjunction with the accompanying drawings, in which.

DETAILED DESCRIPTION OF THE DRAWINGS

Figure 1:
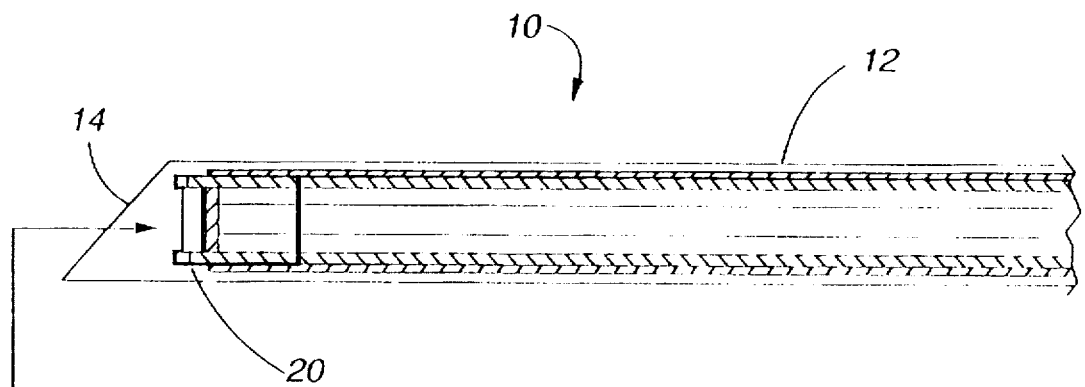
FIGS. 1 and 2 provide sectional views of an interrogation device embodying the present invention.
Figure 2:
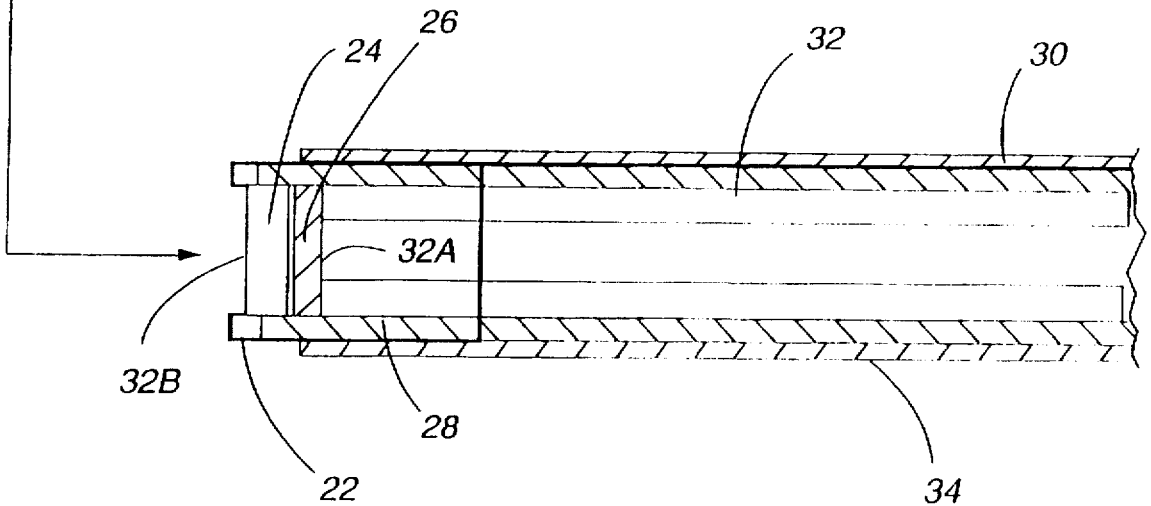

The present invention relates to an interrogation device which overcomes many of the disadvantages found in the prior art. Referring to FIG. 1 and FIG. 2, an interrogation device embodying the present invention is illustrated. The interrogation device 10 is formed by a PZTA 5 crystal 24 mounted on the tip of an electrically conductive support rod 32 with the distal tip of the support rod surrounded by an electrically conductive nerve stimulator electrode 22. The needle guide 12 is generally cylindrical with a sharpened open end 14. Open end 14 can be provided with a suitable bevel using either a B-bevel or regular bevel needle. The doppler directed nerve stimulator electrode 20 is maintained in retracted position as shown in FIG. 1 during insertion. The relatively smaller diameter of the Doppler probe with respect to the inner diameter of the guide needle creates an open annular region through which fluid can flow with minimal resistance. The guide needle 12 is filled with both an acoustically and electrically conductive fluid such as 0.9 percent (%) sodium chloride.

Figure 3:
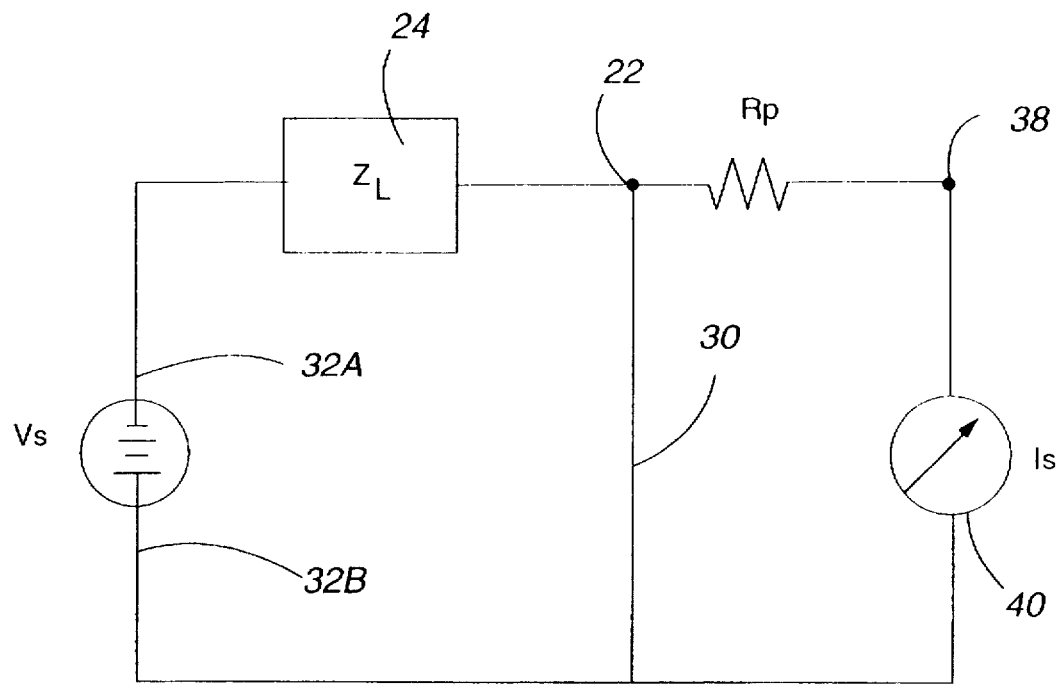
FIG. 3 provides a schematic diagram of the control system.

FIGS. 2 and 3 provide a sectional view of the assembled nerve stimulator electrode and driver circuit respectively. An electrically conductive electrode 22 is attached to the end of the support rod 32 external to the insulating layer 28 and connected to a conductive wire 30 that extends to a wire harness at the base of the support rod. The electrode 22 is connected to a variable output current source 40 by connector 30 shown in FIG. 2 and FIG. 3. The remainder of the nerve stimulator circuit is completed through either a separate AgCl electrode 38 attached to the patient, schematically depicted as $R_p$ the resistance of the patient in FIG. 3, or insulating the inner annulus of the guide needle and using a bipolar nerve stimulator design FIG. 5. The ultrasound PZTA 5 circuit is formed by attaching crystal 24 by a low impedance silver epoxy connection 26 to support rod 32. The crystal and support rod combination are surrounded at the distal end by electrode 22, a generally cylindrical shaped conductive material. The electrode is secured to the support rod by a nonconductive epoxy. This epoxy forms the first insulating layer 28. A second insulating layer using a non-conductive epoxy is formed around the support rod and electrode assembly 34. A wire is then attached to the electrode and extends to the base of the support rod as depicted by conductive wire 30. The wire and conductive support rod are attached separately into a wiring harness which is then integrated into the electrical circuitry as shown in FIG. 3. The connection between the voltage source $V_s$ and proximal surface of the crystal 24, or the silver epoxy connection 26, is depicted at 32a. The connection between the voltage source $V_s$ and the distal surface of the crystal 24 is depicted at 32b. This latter connection can be achieved by a direct connection between the electrode 22 and distal surface of the crystal 24, or by using the conductive properties of the 0.9% NaCl solution in contact with the distal surface of the crystal 24 and electrode 22.

Figure 5:
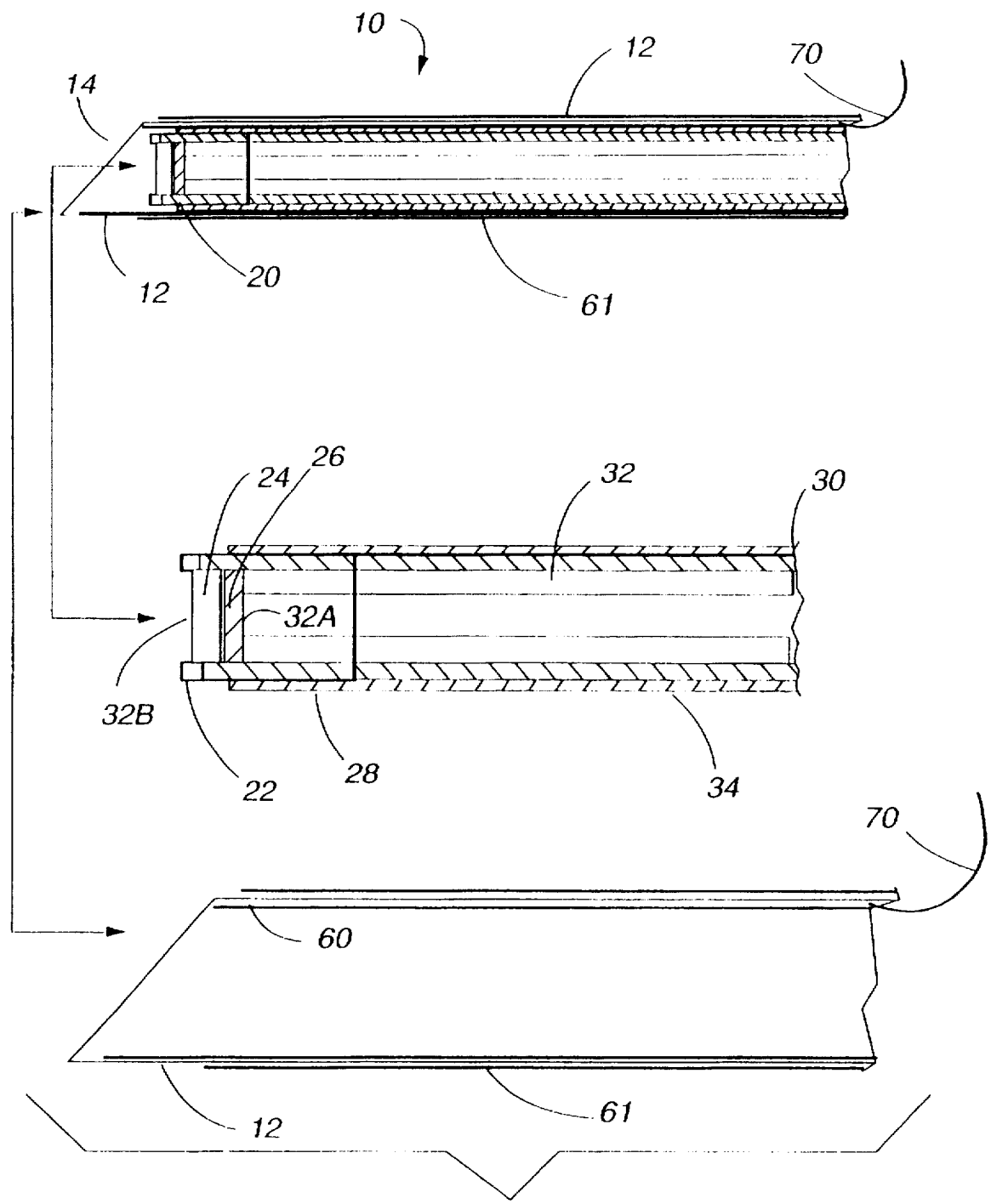
FIG. 5 provides sectional views of an interrogation device embodying a bipolar nerve stimulator embodiment of the present invention.

The bipolar Doppler ultrasound directed nerve stimulator electrode is depicted in FIG. 5. Needle guide 12 is insulated internally with a high impedance insulation 60 such as a nonconductive epoxy. The exterior of needle guide 12 is also insulated except for an area near the tip equal in surface area to the electrode surface area 22. Needle guide 12 is then attached through electrical connection and wiring 70 to current driver circuitry 40 as depicted in FIG. 3.

The electrode can be formed of 20 gauge 304 steel hypodermic tubing. The support rod can be 22 gauge steel hypodermic tubing. The ultrasound transducer can be a ceramic crystal such as the PZTA 5 crystal supplied by Valpey Fischer Company of Hopkington, Mass. or may be a piezoelectric polymer such as PVDF.

Figure 4:
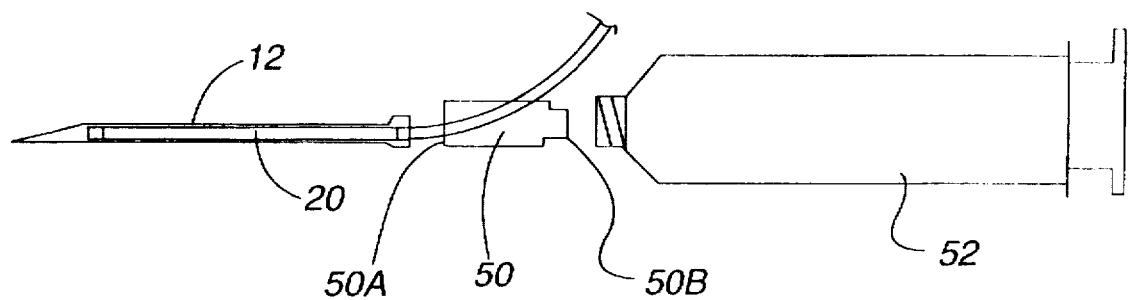
FIG. 4 is an exploded view of the puncture needle, luer lock, and syringe.

FIG. 4 illustrates the Doppler guided nerve stimulator electrode and needle guide 12 attached to a syringe 52 by a luer lock connection 50. The luer lock 50 is a cylindrical connector with connection means at both ends. The needle guide 12 is connected to a first end 50a of the luer lock. A syringe 52 is connected to a second end 50b of the luer lock. An anesthetic or other suitable solution or medicine can be held in the reservoir or the syringe. After the assembly is positioned and the neurovascular bundle punctured, the luer lock can be disconnected allowing the Doppler guided nerve stimulator electrode to be removed from the guide needle. One or more syringes can then be reattached and anesthetic administered through the guide needle.

To use the Doppler guided electrode, the signal processing electronics and current stimulator circuitry are connected to the base of the trocar through a wire harness. The needle guide is inserted under the skin and flushed with a conductive solution, preferably 0.9% NaCl solution. The guide is aimed in the direction of maximal doppler signal and advanced toward that signal. The artery or vein in the neurovascular bundle reflects an ultrasound pulse emitted by the crystal which the piezoelectric crystal receives and converts into a voltage difference. The signal processing electronics then convert this voltage difference into a detectable signal. Simultaneously, the nerve stimulator electrode conducts a current through the tip of the guide needle into the surrounding tissue through the electrically conductive solution. Passage of the tip of the needle guide into the neurovascular bundle can often be appreciated by an abrupt, short high frequency doppler signal. The intensity of this signal is enhanced by the use of "B" bevel pointed needle guide. This same needle bevel also tends to occlude and collapse the arterial or venous signal before puncture. In addition to the localizing doppler signals, the stimulating electrode signals close proximity to the nerve by the appearance of a muscle twitch. Final confirmation of the needle guide within the neurovascular bundle is found by removal of the trocar, infusion of an appropriate amount of local anesthetic, replacement of the trocar, and a visibly reduced muscle twitch to repeated nerve stimulation within a short period of time. Current output through the nerve stimulator including current pulse width, amperage and stimulus frequency are as described in "Electrical Characteristics of Peripheral Nerve Stimulators," by D. J. Ford et al., in Regional Anesthesia, v. 9, no. 2, 73–77.

Although preferred embodiments of the present invention have been described in the foregoing detailed description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements.

I claim:

1. A method of locating a nerve in a body, said nerve associated with a vessel having flowing blood cells, said method comprising the steps of:

(a) penetrating the body with a guide needle having an electrode contained therein, (b) guiding said needle into the body in response to a detector signal triggered by an ultrasound means within said electrode; and (c) guiding said needle to a position proximate the nerve in response to a predetermined muscle response from a stimulating signal emitted by said electrode.

2. The method of claim 1 further comprises:

(d) halting the movement of the guide needle when said detector signal diminishes.

3. The method of claim 1 further comprises:

(d) injecting a substance through said needle into contact with the nerve.

4. The method of claim 3 wherein step of injecting further comprises injecting an anesthetic into contact with said nerve.

5. The method of claim 1 further comprises removing said electrode from said guide needle.

6. The method of claim 5 further comprises inserting a medical instrument in said guide needle.

7. The method of claim 6 where said medical instrument is a guide wire.

8. The method of claim 1 wherein the nerve and vessel are contained within a neurovascular bundle, further comprising the step of:

(d) puncturing the bundle with said needle.

9. The method of claim 8 further comprising:

(e) injecting a substance into the bundle through said needle.

* * * * *